United States Patent
Chalupper

(10) Patent No.: US 11,433,236 B2
(45) Date of Patent: Sep. 6, 2022

(54) SYSTEMS AND METHODS FOR OPTIMIZING SPECTRAL RESOLUTION FOR A HEARING SYSTEM

(71) Applicant: Advanced Bionics AG, Staefa (CH)

(72) Inventor: Josef Chalupper, Paunzhausen (DE)

(73) Assignee: Advanced Bionics AG, Staefa (CH)

( * ) Notice: Subject to any disclaimer, the term of this patent is extended or adjusted under 35 U.S.C. 154(b) by 452 days.

(21) Appl. No.: 16/525,841

(22) Filed: Jul. 30, 2019

(65) Prior Publication Data
US 2021/0031038 A1 Feb. 4, 2021

(51) Int. Cl.
*A61N 1/36* (2006.01)
*A61N 1/05* (2006.01)

(52) U.S. Cl.
CPC ....... *A61N 1/36039* (2017.08); *A61N 1/0541* (2013.01)

(58) Field of Classification Search
CPC .............. A61N 1/36039; A61N 1/0541; A61N 1/36036; A61N 1/36038; A61B 5/121
See application file for complete search history.

(56) References Cited

U.S. PATENT DOCUMENTS

| | | | | |
|---|---|---|---|---|
| 2010/0280307 A1* | 11/2010 | Lineaweaver | ..... | A61N 1/36038 600/25 |
| 2011/0238176 A1 | 9/2011 | Bradley et al. | | |
| 2015/0088225 A1* | 3/2015 | Noble | ..... | G06T 7/149 607/57 |
| 2020/0068324 A1* | 2/2020 | Perscheid | ..... | H04R 25/30 |

FOREIGN PATENT DOCUMENTS

| | | | | |
|---|---|---|---|---|
| WO | WO-2019142072 A1 * | 7/2019 | ........... | H04R 25/554 |
| WO | WO-2019186373 A1 * | 10/2019 | ............... | A61B 5/24 |

OTHER PUBLICATIONS

Nogueira et al, "Design and Evaluation of a Cochlear Implant Strategy Based on a "Phantom" channel" Mar. 25, 2015. PLos One pp. 1-25 (Year: 2015).*

* cited by examiner

*Primary Examiner* — Gary Jackson
*Assistant Examiner* — Sebastian X Lukjan
(74) *Attorney, Agent, or Firm* — ALG Intellectual Property, LLC

(57) ABSTRACT

An exemplary sound processor is configured to maintain data representative of a frequency allocation table that maps frequencies in an upper region of an audible frequency range to a plurality of electrodes located within a cochlea of the first ear, receive an audio signal, direct a cochlear implant to apply standard electrical stimulation representative of frequencies in the audio signal that are within the upper region to the cochlea of the first ear by way of the plurality of electrodes in accordance with the frequency allocation table, and direct the cochlear implant to apply phantom electrical stimulation representative of frequencies in the audio signal that are within a lower region of the audible frequency range to the cochlea of the first ear by way of a most apical electrode and one or more compensating electrodes included in the plurality of electrodes in accordance with a phantom electrode stimulation configuration.

20 Claims, 12 Drawing Sheets

SYSTEMS AND METHODS FOR OPTIMIZING SPECTRAL RESOLUTION FOR A HEARING SYSTEM

BACKGROUND INFORMATION

A cochlear implant system conventionally provides electrical stimulation representative of audio content in accordance with a frequency allocation table that maps frequencies within an audible frequency range to a plurality of electrodes located within a recipient's cochlea. For example, to present audio content having a certain frequency to the recipient, the cochlear implant system provides electrical stimulation by way of a certain electrode to which the certain frequency has been mapped in a frequency allocation table.

Conventionally, frequencies within the audible frequency range that are below a place pitch of the most apical electrode (i.e., below a frequency that corresponds to a position within the cochlea at which the most apical electrode is located) are mapped to the most apical electrode in the frequency allocation table. This allows these relatively low frequencies to be presented to a recipient of a cochlear implant system. However, such a mapping disadvantageously increases the spectral distance between each of the mapped electrodes, thereby reducing spectral resolution for the cochlear implant system (e.g., by reducing the ability of the recipient to distinguish between frequencies represented by electrical stimulation applied by way of the electrodes).

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1A:
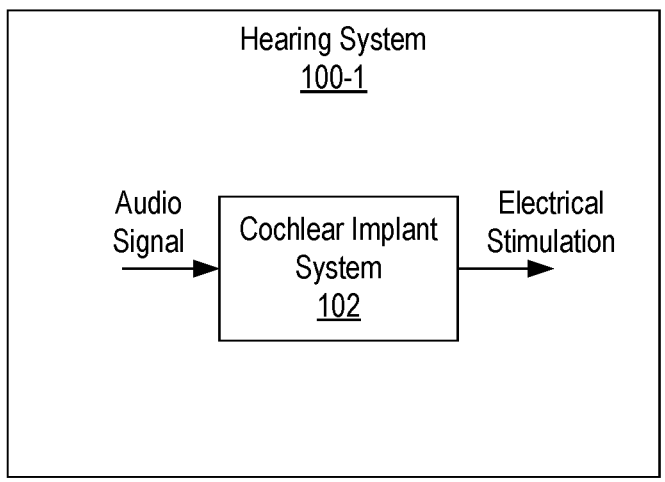
FIGS. 1A-1C illustrate exemplary hearing systems according to principles described herein.

Systems and methods for optimizing spectral resolution for a hearing system are described herein. For example, a system may include a sound processor associated with a first ear of a recipient and configured to control an operation of a cochlear implant associated with the first ear. The sound processor may be configured to maintain data representative of a frequency allocation table that maps frequencies in an upper region of an audible frequency range to a plurality of electrodes located within a cochlea of the first ear. The upper region of the audible frequency range includes frequencies above and including a cut-off frequency. A lower region of the audible frequency range includes frequencies below the cut-off frequency. As described herein, the frequencies in the lower region are not included in the frequency allocation table. Accordingly, when the sound processor receives an audio signal representative of audio content presented to the recipient, the sound processor may direct a cochlear implant to apply standard electrical stimulation representative of frequencies in the audio signal that are within the upper region of the audible frequency range to the cochlea of the first ear by way of the plurality of electrodes in accordance with the frequency allocation table. For frequencies in the audio signal that are in the lower region of the audible frequency range, the sound processor may direct the cochlear implant to apply phantom electrical stimulation representative of these frequencies to the cochlea of the first ear by way of a most apical electrode and one or more compensating electrodes in accordance with a phantom electrode stimulation configuration.

As used herein, "standard electrical stimulation" applied by way of an electrode refers to electrical stimulation configured to convey (e.g., cause a recipient to perceive) a frequency mapped to the electrode in a frequency allocation table. For example, the standard electrical stimulation may be focused only to a location within the cochlear tissue proximate (e.g., nearby, immediately surrounding, etc.) a location where the electrode is positioned. The standard electrical stimulation may additionally or alternatively be focused to a location within the cochlear tissue that is in between locations that correspond to where two or more electrodes are positioned (e.g., by using current steering).

In contrast, "phantom electrical stimulation" is configured to convey (e.g., cause a recipient to perceive) a frequency that is not mapped to an electrode in the frequency allocation table. For example, in accordance with the systems and methods described herein, phantom electrical stimulation applied by way of the most apical electrode and one or more compensating electrodes adjacent to the most apical electrode may convey a frequency or pitch that is lower than the frequency mapped to the most apical electrode in the frequency allocation table.

By not including the frequencies in the lower region of the audible frequency range in the frequency allocation table and instead conveying these frequencies using phantom electrical stimulation, the systems and methods described herein may increase the number of electrodes per octave in the upper region of the audible frequency range. This may facilitate increased spectral resolution in this region for a recipient of the cochlear implant system. Moreover, by using phantom electrical stimulation to convey frequencies in the lower frequency region of the audible frequency range (and, in some cases, a hearing device configured to provide acoustic stimulation representative of these frequencies), sound quality may be maintained or enhanced compared to conventional cochlear implant system configurations.

Figure 1B:
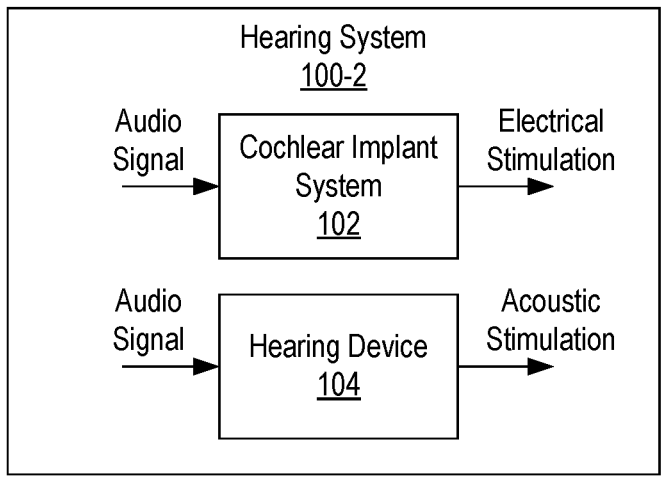
Figure 1C:
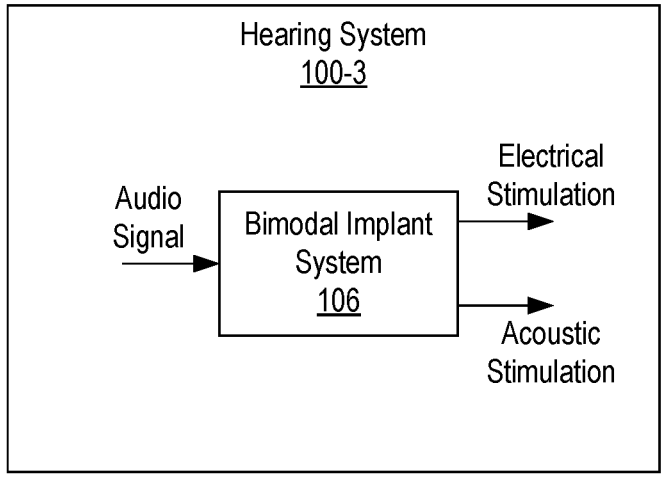

FIGS. 1A-1C illustrate exemplary hearing systems 100 (i.e., hearing systems 100-1 through 100-3) that may be configured to implement the systems and methods described herein.

As shown in FIG. 1A, hearing system 100-1 includes a cochlear implant system 102 configured to receive an audio signal and apply electrical stimulation representative of the audio signal to a recipient of cochlear implant system 102. An exemplary cochlear implant system 102 is described herein. In the configuration shown in FIG. 1A, cochlear implant system 102 is associated with a single ear of the recipient and is the only hearing prosthesis included in hearing system 100-1. Hence, hearing system 100-1 may be referred to as a unilateral and/or single mode hearing system.

As shown in FIG. 1B, hearing system 100-2 includes both cochlear implant system 102 and a hearing device 104. As described in FIG. 1A, cochlear implant system 102 is configured to receive an audio signal and apply electrical stimulation representative of the audio signal to a recipient of cochlear implant system 102. Hearing device 104 may be configured to receive the same audio signal (or a different audio signal representative of the same audio content represented by the audio signal received by cochlear implant system 102) and apply acoustic stimulation representative of the audio signal to the recipient. An exemplary hearing device 104 configured to provide acoustic stimulation is described herein. In the configuration shown in FIG. 1B, cochlear implant system 102 was associated with a first ear of the recipient and hearing device 104 is associated with a second ear of the recipient. Hence, hearing system 100-2 may be referred to as a bimodal hearing system.

As shown in FIG. 1C, hearing system 100-3 includes a bimodal implant system 106 configured to receive an audio signal and apply both electrical and acoustic stimulation representative of the audio signal to a recipient. Bimodal implant system 106 is associated with a single ear of the recipient and therefore provides the electrical and acoustic stimulation to the same ear. An exemplary bimodal implant system 106 is described herein.

A bimodal hearing system, such as hearing systems 100-2 and 100-3, may be useful in cases where the recipient has some degree of residual hearing in a lower frequency region. This will be described in more detail below.

Figure 2:
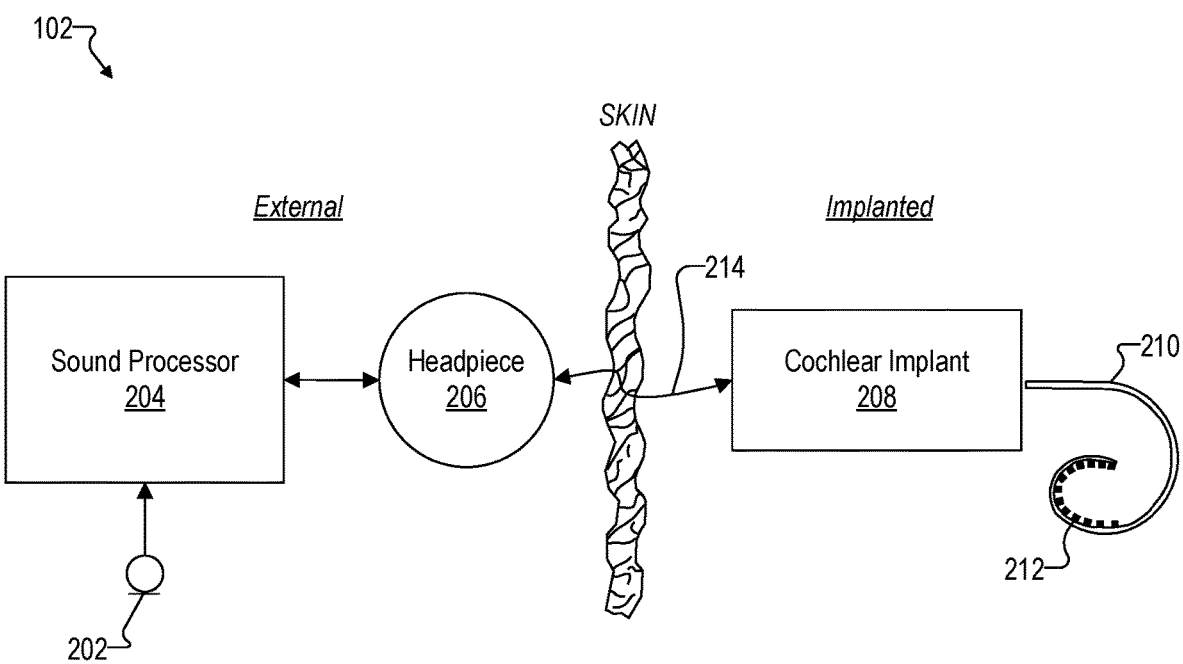
FIG. 2 illustrates an exemplary implementation of a cochlear implant system according to principles described herein.

FIG. 2 illustrates an exemplary implementation of cochlear implant system 102. As shown, cochlear implant system 102 may include a microphone 202, a sound processor 204, a headpiece 206 having a coil disposed therein, a cochlear implant 208, and an electrode lead 210. Electrode lead 210 may include an array of electrodes 212 disposed on a distal portion of electrode lead 210 and that are configured to be inserted into a cochlea of a recipient to stimulate the cochlea when the distal portion of electrode lead 210 is inserted into the cochlea. One or more other electrodes (e.g., including a ground electrode, not explicitly shown) may also be disposed on other parts of electrode lead 210 (e.g., on a proximal portion of electrode lead 210) to, for example, provide a current return path for stimulation current generated by electrodes 212 and to remain external to the cochlea after electrode lead 210 is inserted into the cochlea. As shown, electrode lead 210 may be pre-curved so as to properly fit within the spiral shape of the cochlea. Additional or alternative components may be included within cochlear implant system 102 as may serve a particular implementation.

As shown, cochlear implant system 102 may include various components configured to be located external to a recipient including, but not limited to, microphone 202, sound processor 204, and headpiece 206. Cochlear implant system 102 may further include various components configured to be implanted within the recipient including, but not limited to, cochlear implant 208 and electrode lead 210.

Microphone 202 may be configured to detect audio signals presented to the user. Microphone 202 may be implemented in any suitable manner. For example, microphone 202 may include a microphone that is configured to be placed within the concha of the ear near the entrance to the ear canal, such as a T-MIC™ microphone from Advanced Bionics. Such a microphone may be held within the concha of the ear near the entrance of the ear canal during normal operation by a boom or stalk that is attached to an ear hook configured to be selectively attached to sound processor 204. Additionally or alternatively, microphone 202 may be implemented by one or more microphones disposed within headpiece 206, one or more microphones disposed within sound processor 204, one or more beam-forming microphones, and/or any other suitable microphone as may serve a particular implementation.

Sound processor 204 may be configured to direct cochlear implant 208 to generate and apply electrical stimulation (also referred to herein as "stimulation current") representative of one or more audio signals (e.g., one or more audio signals detected by microphone 202, input by way of an auxiliary audio input port, input by way of a clinician's programming interface (CPI) device, etc.) to one or more stimulation sites associated with an auditory pathway (e.g., the auditory nerve) of the recipient. Exemplary stimulation sites include, but are not limited to, one or more locations within the cochlea, the cochlear nucleus, the inferior colliculus, and/or any other nuclei in the auditory pathway. To this end, sound processor 204 may process the one or more audio signals in accordance with a selected sound processing strategy or program to generate appropriate stimulation parameters for controlling cochlear implant 208. Sound processor 204 may be housed within any suitable housing (e.g., a behind-the-ear ("BTE") unit, a body worn device, headpiece 206, and/or any other sound processing unit as may serve a particular implementation).

In some examples, sound processor 204 may wirelessly transmit stimulation parameters (e.g., in the form of data words included in a forward telemetry sequence) and/or power signals to cochlear implant 208 by way of a wireless communication link 214 between headpiece 206 and cochlear implant 208 (e.g., a wireless link between a coil disposed within headpiece 206 and a coil physically coupled to cochlear implant 208). It will be understood that communication link 214 may include a bi-directional communication link and/or one or more dedicated uni-directional communication links.

Headpiece 206 may be communicatively coupled to sound processor 204 and may include an external antenna (e.g., a coil and/or one or more wireless communication components) configured to facilitate selective wireless coupling of sound processor 204 to cochlear implant 208. Headpiece 206 may additionally or alternatively be used to selectively and wirelessly couple any other external device to cochlear implant 208. To this end, headpiece 206 may be configured to be affixed to the recipient's head and positioned such that the external antenna housed within headpiece 206 is communicatively coupled to a corresponding implantable antenna (which may also be implemented by a coil and/or one or more wireless communication components) included within or otherwise associated with cochlear implant 208. In this manner, stimulation parameters and/or power signals may be wirelessly transmitted between sound processor 204 and cochlear implant 208 via communication link 214.

Cochlear implant 208 may include any suitable type of implantable stimulator. For example, cochlear implant 208 may be implemented by an implantable cochlear stimulator. Additionally or alternatively, cochlear implant 208 may include a brainstem implant and/or any other type of cochlear implant that may be implanted within a recipient and configured to apply stimulation to one or more stimulation sites located along an auditory pathway of a recipient.

In some examples, cochlear implant 208 may be configured to generate electrical stimulation representative of an audio signal processed by sound processor 204 (e.g., an audio signal detected by microphone 202) in accordance with one or more stimulation parameters transmitted thereto by sound processor 204. Cochlear implant 208 may be further configured to apply the electrical stimulation to one or more stimulation sites (e.g., one or more intracochlear regions) within the recipient via electrodes 212 disposed along electrode lead 210. In some examples, cochlear implant 208 may include a plurality of independent current sources each associated with a channel defined by one or more of electrodes 212. In this manner, different stimulation current levels may be applied to multiple stimulation sites simultaneously by way of multiple electrodes 212.

Figure 3:
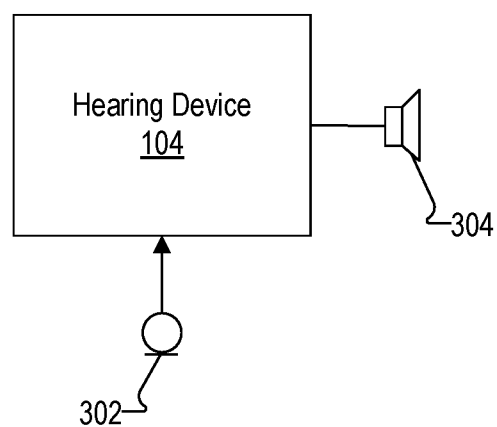
FIG. 3 illustrates an exemplary implementation of a hearing device according to principles described herein.

FIG. 3 illustrates an exemplary implementation of hearing device 104. As shown, hearing device may be communicatively coupled to a microphone 302 configured to generate an audio signal representative of audio content presented to a recipient of hearing device 14. A receiver 304 (also called a speaker or loudspeaker) is also communicatively coupled to hearing device 104. In this configuration, hearing device 104 may provide acoustic stimulation representative of an audio signal output by microphone 302 by way of receiver 304. While microphone 302 and speaker 304 are shown to be communicatively coupled to hearing device 104, it will be recognized that microphone 302 and speaker 304 may alternatively be integrated into hearing device 104.

Hearing device 104 may be implemented by any suitable device configured to provide acoustic stimulation. For example, hearing device 104 may be implemented by a hearing aid configured to amplify sound presented to a recipient of hearing device 104.

Figure 4:
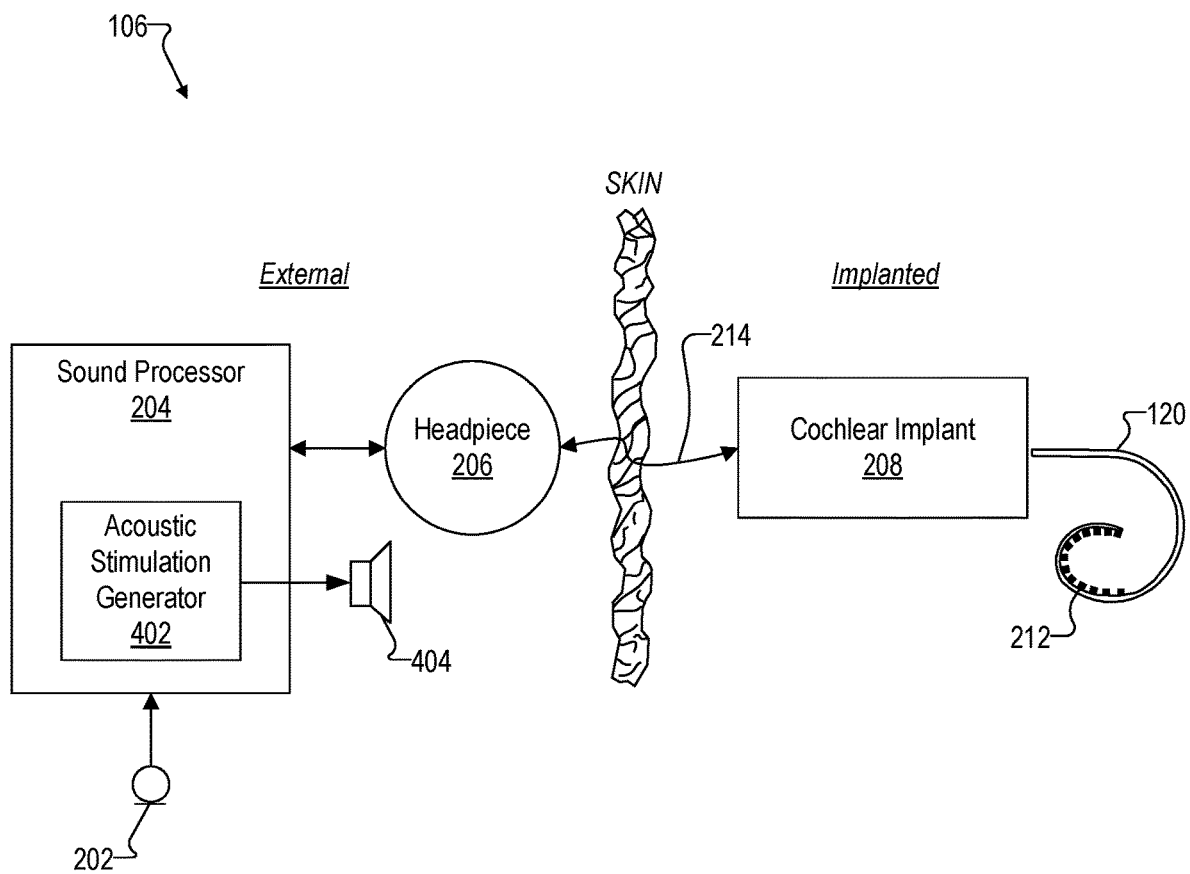
FIG. 4 illustrates an exemplary implementation of a bimodal implant system according to principles described herein.

FIG. 4 illustrates an exemplary implementation of bimodal implant system 106. As shown, bimodal implant system 106 is similar to cochlear implant system 102. However, bimodal implant system 106 further includes an acoustic stimulation generator 402 configured to generate acoustic stimulation representative of an audio signal received by sound processor 204. Sound processor 204 may be configured to apply the acoustic stimulation to the recipient by way of a receiver 404. Hence, bimodal implant system 106 is configured to provide both acoustic stimulation and electrical stimulation representative of audio content presented to the recipient of bimodal implant system 106.

Figure 5:
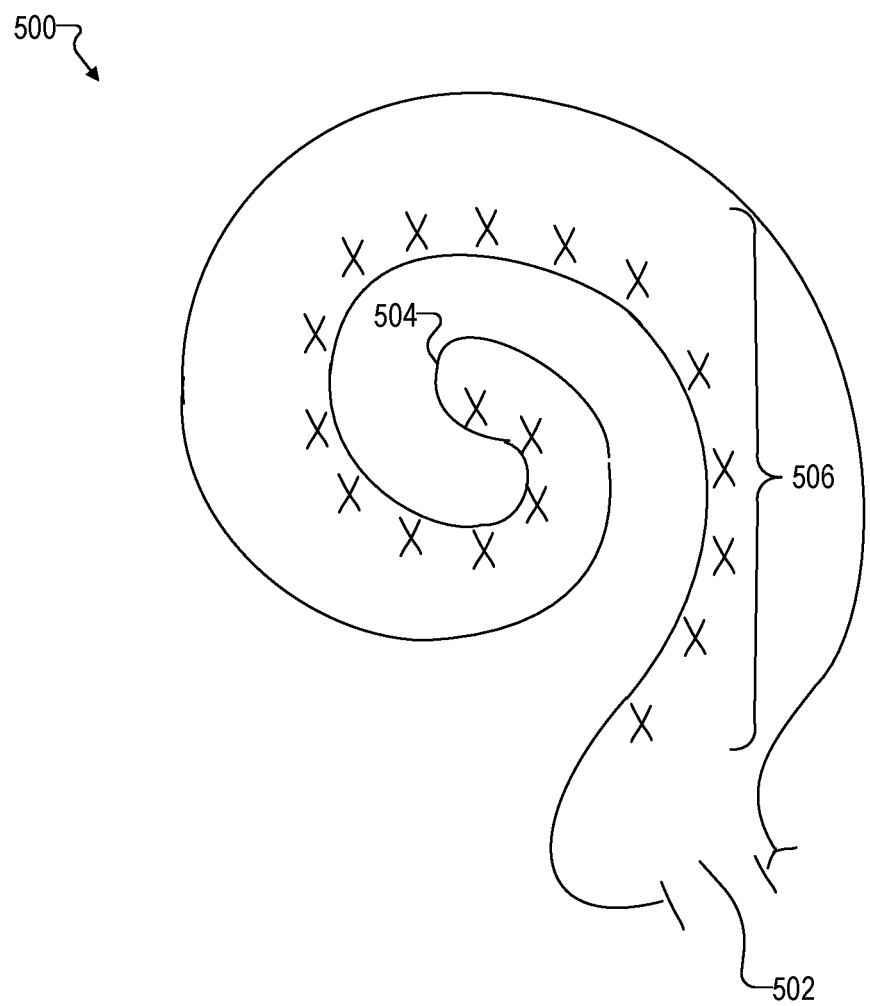
FIG. 5 illustrates a schematic structure of the human cochlea according to principles described herein.

FIG. 5 illustrates a schematic structure of the human cochlea 500 into which electrode lead 110 may be inserted. As shown in FIG. 5, cochlea 500 is in the shape of a spiral beginning at a base 502 and ending at an apex 504. Within cochlea 500 resides auditory nerve tissue 506, which is denoted by Xs in FIG. 5. The auditory nerve tissue 506 is organized within the cochlea 500 in a tonotopic manner. Relatively low frequencies are encoded at or near the apex 504 of the cochlea 500 (referred to as an "apical region") while relatively high frequencies are encoded at or near the base 502 (referred to as a "basal region"). Hence, electrical stimulation applied by way of electrodes disposed within the apical region (i.e., "apical electrodes") may result in the recipient perceiving relatively low frequencies and electrical stimulation applied by way of electrodes disposed within the basal region (i.e., "basal electrodes") may result in the recipient perceiving relatively high frequencies. The delineation between the apical and basal electrodes on a particular electrode lead may vary depending on the insertion depth of the electrode lead, the anatomy of the recipient's cochlea, and/or any other factor as may serve a particular implementation.

Figure 6:
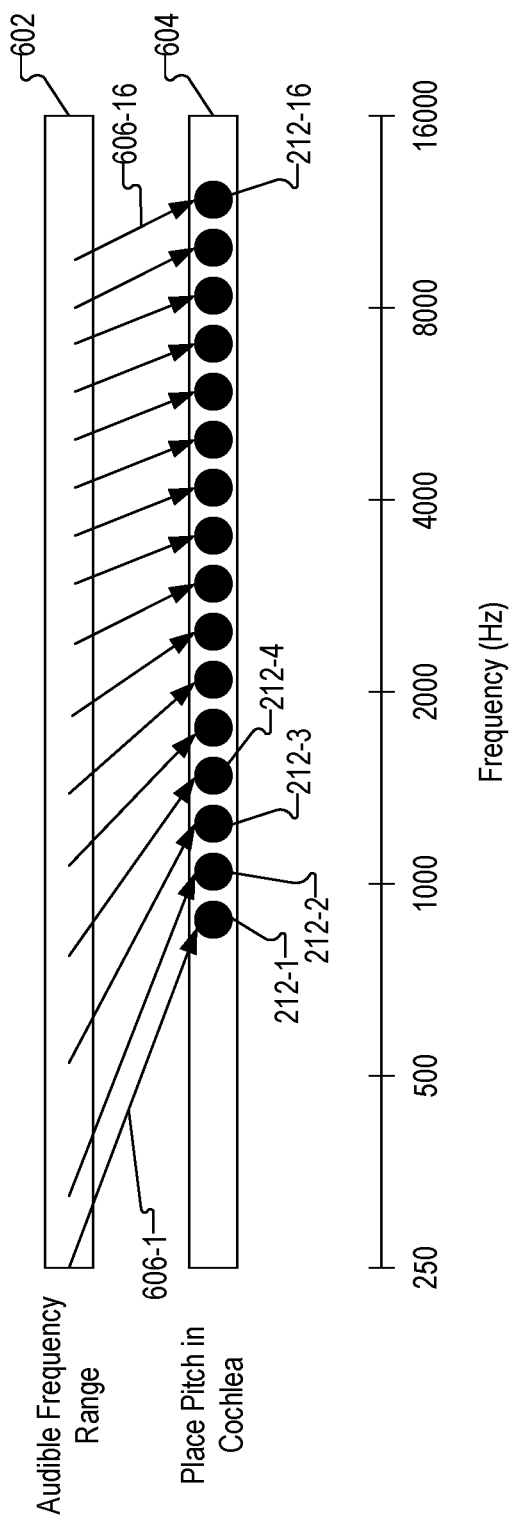
FIGS. 6-7 illustrate exemplary mappings between frequencies in an audible frequency range and electrodes that may be defined by a frequency allocation table according to principles described herein.

FIG. 6 illustrates an exemplary mapping between frequencies in an audible frequency range 602 and electrodes 212 (i.e., electrodes 212-1 through 212-16) that may be defined by a frequency allocation table. As described herein, the frequency allocation table may be used by sound processor 202 to direct cochlear implant 208 to apply electrical stimulation representative of various frequencies included in an audio signal.

For purposes of this example, audible frequency range 602 includes a range of frequencies including and in between 250 Hz and 16 kHz. Each of these frequencies may be audible to a person with normal hearing. In some examples, the frequencies in audible frequency range 602 are also audible to a hearing impaired recipient of a hearing system, such as one of the hearing systems 100 described herein. It will be recognized that some frequencies lower than 250 Hz and some frequencies above 16 kHz may be included in audible frequency range 602, depending on the particular person and/or listening scenario as may serve a particular implementation.

In the example of FIG. 6, electrode 212-1 is the most apical electrode on electrode lead 210. In other words, electrode 212-1 is the most distally located electrode on electrode lead 210 such that when electrode lead 210 is inserted into the cochlea, electrode 212-1 is located closest to the apex of the cochlea. Electrode 212-16 is the most basal electrode on electrode lead 210. In other words, electrode 212-16 is the most proximally located electrode on electrode lead 210 such that when electrode lead 210 is inserted into the cochlea, electrode 212-16 is located closest to the base of the cochlea.

Once implanted within the cochlea, electrodes 212 may each be located at a different intracochlear location that corresponds to a particular place pitch 604. As used herein, a "place pitch" associated with a particular intracochlear location refers to a frequency that is perceived by the recipient when the intracochlear location is stimulated with electrical stimulation by an electrode 212 at the intracochlear location. For example, as shown, electrode 212-1 is located at an intracochlear location associated with a place pitch of approximately 700 Hz and electrode 212-16 is located at an intracochlear location associated with a place pitch of approximately 14 kHz.

Arrows (e.g., arrow 606-1 through arrow 606-16) represent mappings defined by a frequency allocation table between various frequencies in audible frequency range 602 and electrodes 212. As shown, frequencies in the audible frequency range that are below the place pitch associated with the most apical electrode 212-1 are mapped to electrodes 212-1 through 212-3. Frequencies in the audible frequency range that are greater than the place pitch associated with the most apical electrode 212-1 are mapped to electrodes 212-4 through 212-16. In some examples, multiple frequencies may be mapped to a single electrode 212 or to multiple electrodes 212. For example, intermediate frequencies in between the frequency shown as being mapped to electrode 212-1 and the frequency shown as being mapped to electrode 212-2 may be mapped to one or both of electrodes 212-1 and 212-2. In this example, current steering or some other standard electrical stimulation configuration may be used to convey these intermediate frequencies.

The mapping shown in FIG. 6 disadvantageously increases the spectral distance between each of the mapped electrodes, thereby reducing spectral resolution for cochlear implant system 102 (e.g., by reducing the ability of the recipient to distinguish between frequencies represented by electrical stimulation applied by way of electrodes 212).

Accordingly, in accordance with the systems and methods described herein, only frequencies included in an "upper region" of audible frequency range 602 are mapped to electrodes 212, while frequencies included in a "lower region" of audible frequency range 602 are not mapped to electrodes 212. Hence, as described herein, standard electrical stimulation is not used to convey these lower region frequencies to a recipient of hearing system 100.

Figure 7:
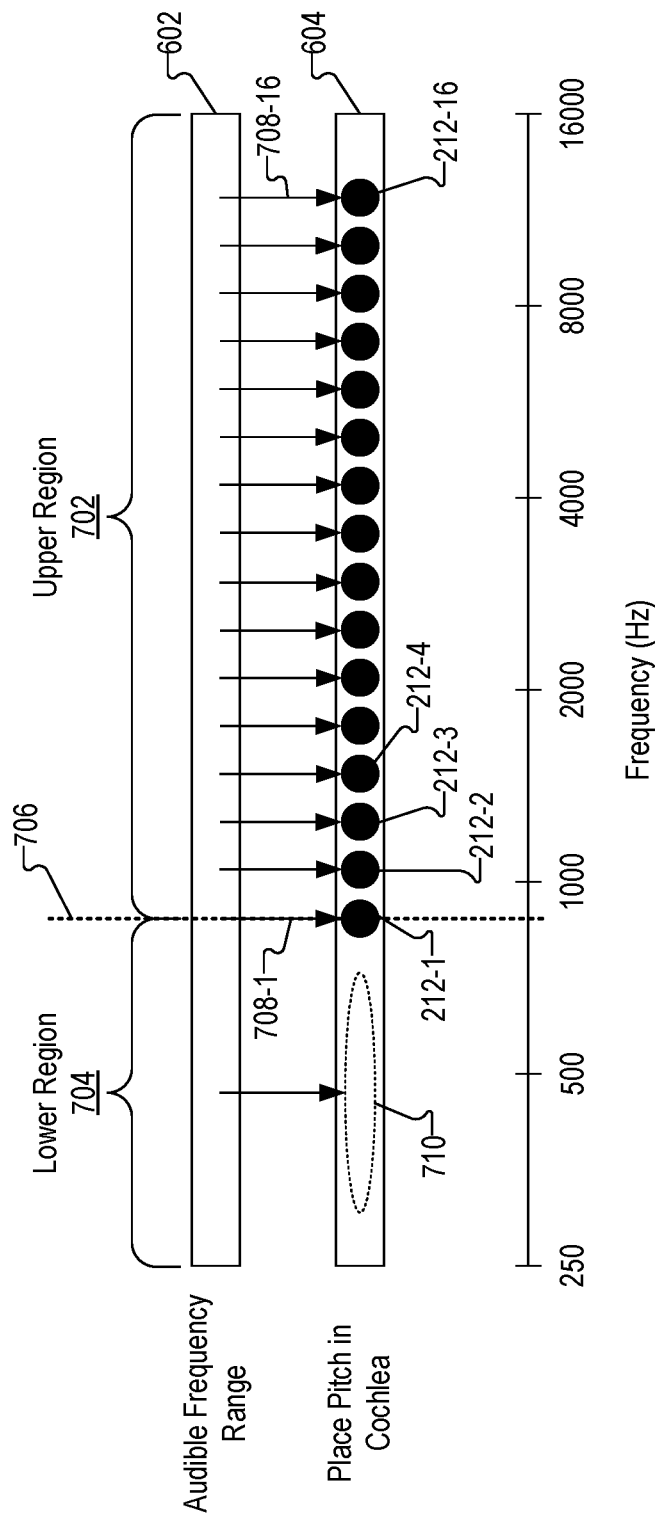

To illustrate, FIG. 7 shows an exemplary mapping between frequencies in audible frequency range 602 and electrodes 212 that may be defined by a frequency allocation table in accordance with the systems and methods described herein. As shown, audible frequency range 602 may be divided into an upper region 702 and a lower region 704. Upper region 702 includes a cutoff frequency 706 and frequencies above cutoff frequency 706. Lower region 704 includes frequencies below cutoff frequency 706. In the example of FIG. 7, the cutoff frequency 706 is approximately 700 Hz. Hence, upper region 702 includes frequencies between and including 700 Hz and 16 kHz, and lower region 702 includes frequencies below 700 Hz.

Cutoff frequency 706 may be set to be any suitable frequency that is greater than a lower bound (e.g., 250 Hz) of audible frequency range 602. In some examples, cutoff frequency 706 is at least a frequency octave above the lower bound of audible frequency range 602 so that phantom electrical stimulation may be used to convey at least the frequency octave to the recipient, as will be described in more detail below. Various ways that may be used to specify cutoff frequency 706 are described herein.

As shown, only the frequencies included in upper region 702 are mapped to electrodes 212. For example, cutoff frequency 706 is mapped to electrode 212-1. Other frequencies in upper region 702 are also mapped to electrodes 212.

In some examples, each electrode 212 is mapped to a frequency equal to a place pitch of the electrode. For example, FIG. 7 shows that a frequency of approximately 700 Hz, which corresponds to a place pitch of electrode 212-1, is mapped to electrode 212-1. Each of the other electrodes 212 is mapped to a frequency equal to its corresponding place pitch, as indicated by the vertical arrows 708-1 through 708-16 in FIG. 7. Any other suitable mapping between frequencies in upper region 702 of audible frequency range 602 to electrodes 212 may be used as may serve a particular implementation.

In this configuration, sound processor 204 may be configured to direct cochlear implant 210 to apply standard electrical stimulation representative of frequencies in an audio signal that are within upper region 702 to a cochlea of a recipient by way of electrodes 212 in accordance with the mapping defined by the frequency allocation table represented in FIG. 7. The standard electrical stimulation may include monopolar stimulation, multipolar (e.g., bipolar) stimulation, current steering, and/or any other type of stimulation other than phantom electrical stimulation.

In contrast, based on the mapping illustrated in FIG. 7, standard electrical stimulation is not used to convey frequencies in lower region 704. Rather, sound processor 204 is configured to direct cochlear implant 210 to convey frequencies in lower region 704 by applying phantom electrical stimulation by way of a phantom stimulation channel 710 in accordance with a phantom electrode stimulation configuration. Phantom stimulation channel 710 comprises the most apical electrode 212-1 and one or more compensating electrodes 212. In some examples, compensating electrodes 212 are adjacent to most apical electrode 212-1 (e.g., electrode 212-2 and/or electrode 212-3).

As described herein, phantom electrical stimulation is configured to convey (e.g., cause a recipient to perceive) a frequency that is not mapped to an electrode in a frequency allocation table (e.g., in a frequency allocation table that has the mapping illustrated in FIG. 7). For example, phantom electrical stimulation applied by way of most apical electrode 212-1 and one or more compensating electrodes adjacent to the most apical electrode may convey a frequency or pitch that is lower than the frequency mapped to most apical electrode 212-1 in the frequency allocation table.

Sound processor 204 may be configured to direct cochlear implant 110 to apply phantom electrical stimulation by directing cochlear implant 210 to apply a main stimulation current by way of the most apical electrode 212-1, directing cochlear implant 210 to concurrently apply, while the main stimulation current is being applied by way of the most apical electrode 212-1, a compensation stimulation current by way of the one or more compensating electrodes (e.g., electrodes 212-2 and/or 212-3), and optimizing an amount of the compensation stimulation current to result in the frequencies in the audio signal that are within lower region 704 of audible frequency range 602 being presented to the recipient. Phantom electrical stimulation is described in more detail in U.S. Pat. No. 9,056,205, the contents of which are incorporated herein by reference in their entirety.

Figure 8:
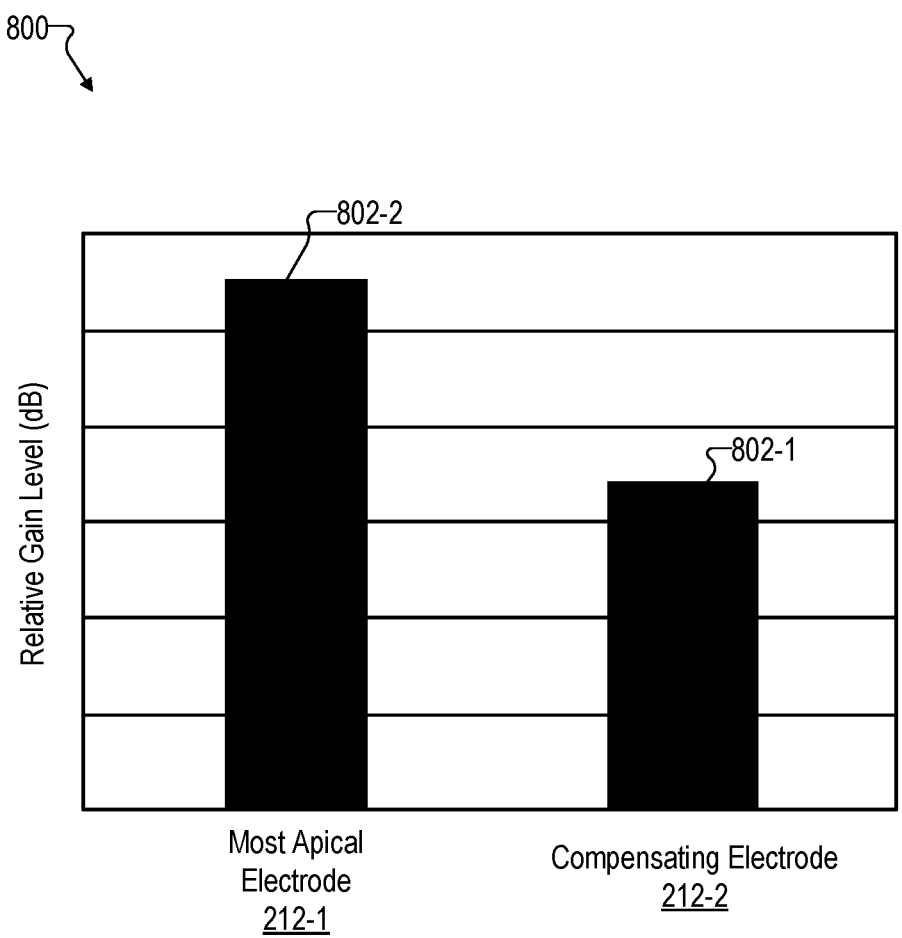
FIG. 8 illustrates exemplary gain parameters that may be employed to implement a phantom electrical stimulation configuration according to principles described herein.

FIG. 8 illustrates exemplary gain parameters that may be employed to implement a phantom electrical stimulation configuration in accordance with the systems and methods described herein. In this example, electrode 212-1 is the sole compensating electrode. As depicted in FIG. 8, sound processor 204 may adjust relative gain levels of gain parameters 802-1 and 802-2 corresponding to compensating electrode 212-2 and most apical electrode 212-1, respectively, such that a frequency perceived by a recipient is substantially identical to a frequency in an audio signal that is within lower region 704. Gain parameter 802-1 may represent a level of compensation stimulation current applied by way of compensating electrode 212-1 and gain parameter 802-2 may represent a level of main stimulation current applied by way of most apical electrode 212-1.

In some examples, gain parameters 802-1 and 802-2 may be configured in accordance with a selected ratio of compensation stimulation current to main stimulation current corresponding to the particular frequency in the incoming audio signal. Additionally, gain parameters 802-1 and 802-2 may be adjusted such that the total current applied to electrodes 212-1 and 212-2 is substantially at the most comfortable current level. In some examples, the compensation stimulation current is out-of-phase with main current (e.g., by 180 degrees). The compensation stimulation current may additionally or alternatively have a polarity opposite that of the main stimulation current.

Frequencies in lower region 704 of audible frequency range 602 may additionally be conveyed to a recipient in any other suitable manner. For example, in cases where a recipient is associated with bimodal hearing system 100-2, frequencies in lower region 704 of audible frequency range 602 may additionally be conveyed by way of hearing device 104. In these cases, hearing device 104 may receive the same audio signal received by cochlear implant system 102 (e.g., by detecting the audio signal with a microphone and/or receiving the audio signal by way of an auxiliary audio input, etc.) and direct receiver 304 to apply acoustic stimulation representative of the frequencies in the audio signal that are in lower region 704 to the recipient. In this manner, low frequency content may be conveyed to the recipient using both phantom electrical stimulation (at one ear) and acoustic stimulation (at the other ear). This may increase the ability of the recipient to perceive the low frequency content.

As another example, a recipient may be associated with bimodal hearing system 100-3. In this example, in addition to directing cochlear implant 210 to convey frequencies in lower region 704 by applying phantom electrical stimulation way of phantom stimulation channel 710, sound processor 204 may direct receiver 404 to apply acoustic stimulation representative of the frequencies in lower region 704 to the same ear of recipient.

Data representative of a frequency allocation table, such as the frequency allocation table illustrated by the mapping shown in FIG. 7, may be maintained by sound processor 204 in any suitable manner. For example, data representative of a frequency allocation table may be stored by sound processor 204 in memory located within sound processor 204. The data representative of the frequency allocation table may be additionally or alternatively accessed by sound processor 204 in any other suitable manner.

A frequency allocation table may be specified in any suitable manner. For example, sound processor 204 may automatically specify (e.g., modify, update, program, or otherwise set) a frequency allocation table based on one or more characteristics of a recipient, one or more program settings of sound processor 204, and/or any other factor.

Figure 9:
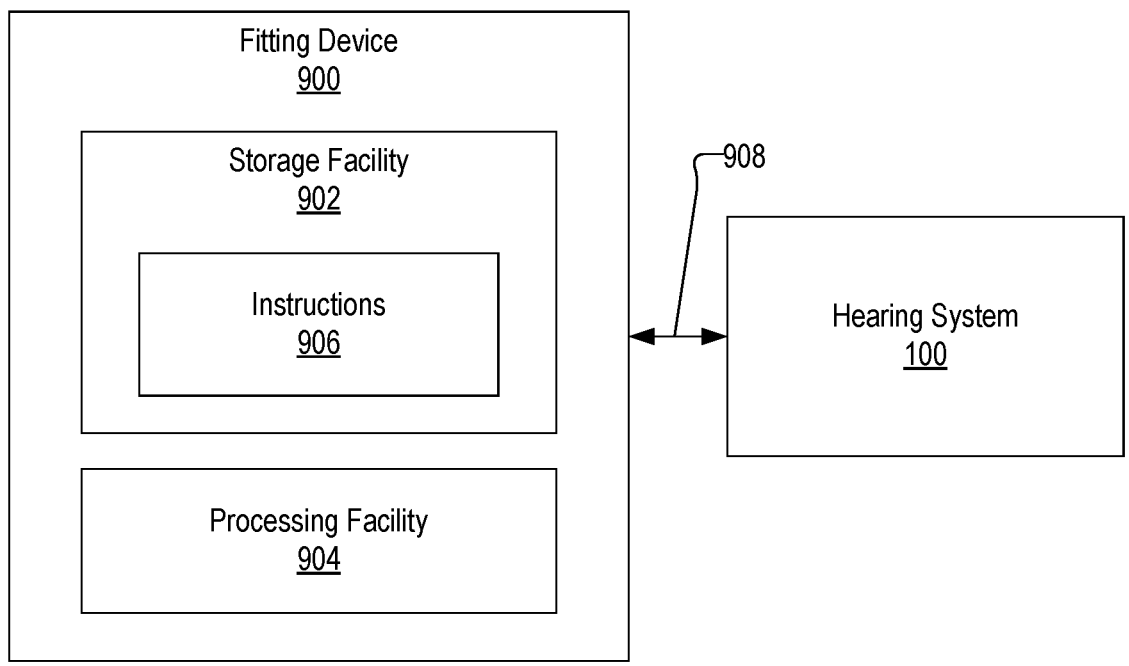
FIG. 9 shows an exemplary configuration in which a fitting device is communicatively coupled to a hearing system according to principles described herein.

A frequency allocation table may additionally or alternatively be specified by a computing device external to sound processor 204. For example, FIG. 9 shows an exemplary configuration in which a fitting device 900 is communicatively coupled to hearing system 100. As described herein, fitting device 900 may be configured to specify a frequency allocation table and transmit data representative of the frequency allocation table to hearing system 100 (e.g., to sound processor 204). Fitting device 900 may be implemented by any suitable computing device, such as a desktop computer, a laptop computer, a tablet computer, a mobile phone, etc.

As shown, fitting device 900 may include, without limitation, a storage facility 902 and a processing facility 904 selectively and communicatively coupled to one another. Facilities 902 and 904 may each include or be implemented by hardware and/or software components (e.g., processors, memories, communication interfaces, instructions stored in memory for execution by the processors, etc.).

Storage facility 902 may maintain (e.g., store) executable data used by processing facility 904 to perform any of the operations described herein. For example, storage facility 902 may store instructions 906 that may be executed by processing facility 904 to perform any of the operations described herein. Instructions 906 may be implemented by any suitable application, software, code, and/or other executable data instance.

Processing facility 904 may be configured to perform (e.g., execute instructions 906 stored in storage facility 902 to perform) various fitting operations with respect to hearing system 100. For example, processing facility 904 may be configured to set one or more parameters that govern an operation of one or more components of hearing system 100.

Fitting device 900 may be selectively and communicatively coupled to hearing system 100 by way of a communication channel 908. For example, fitting device 900 may be connected by way of a wired and/or wireless connection to sound processor 204. While communicatively coupled to hearing system 100, fitting device 900 may transmit data to hearing system 100 (e.g., to sound processor 204). For example, fitting device 900 may transmit data representative of a frequency allocation table to sound processor 204. Sound processor 204 may receive and store the data in any suitable manner.

Fitting device 900 may specify the frequency allocation table in any suitable manner. For example, fitting device 900 may set a value for cutoff frequency 706 and map the cutoff frequency to most apical electrode 212-1. Fitting device 900 may set the value for cutoff frequency 706 in any suitable manner. For example, fitting device 900 may access data representative of a computerized tomography (CT) scan (or other medical imaging modality) of the recipient's cochlea while electrode lead 210 is located within the cochlea. Based on the CT scan, fitting device 900 may identify a place pitch of most apical electrode 212-1 and designate the place pitch as cutoff frequency 706. Fitting device 900 may identify the place pitch of most apical electrode 212-1 based on the CT scan in any suitable manner.

In some examples, fitting device 900 may be configured to specify the frequency allocation table by identifying a frequency region within audible frequency range 602 that has poor spectral resolution for the particular recipient. Fitting device 900 may then map frequencies within this frequency region to multiple electrodes 212.

Figure 10:
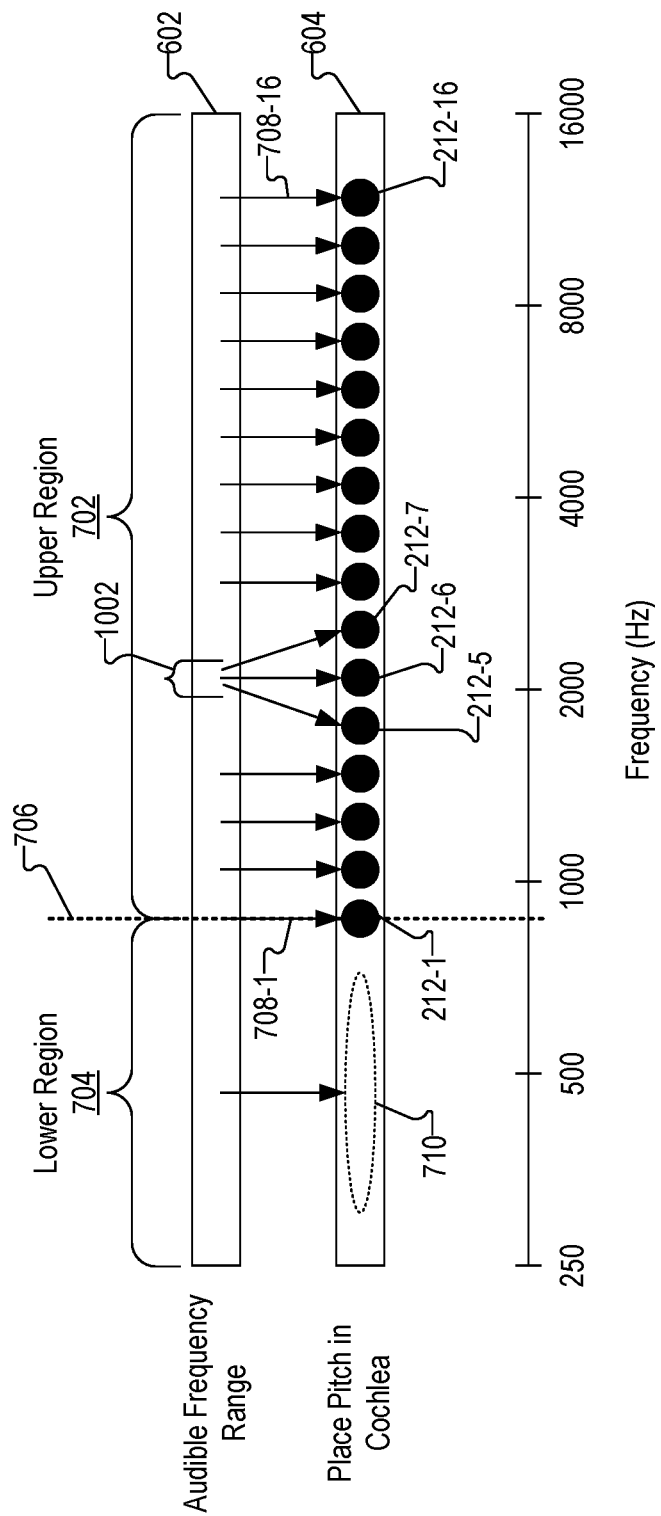
FIG. 10 shows an exemplary mapping of frequencies within an upper region of a audible frequency range to electrodes according to principles described herein.

To illustrate, FIG. 10 shows an exemplary mapping of frequencies within upper region 702 of audible frequency range 602 to electrodes 212. FIG. 10 is similar to FIG. 7, except that in FIG. 10, a frequency region 1002 that has poor spectral resolution for the recipient has been identified. As shown, frequencies in this region 1002 are mapped to more electrodes than they are in FIG. 7. In particular, frequencies within this region 1002 are mapped to electrodes 212-5 through 212-7. In this manner, enhanced spectral resolution may be achieved within regions that have relatively poor native spectral resolution.

Fitting device 900 may be configured to identify a frequency region that has poor spectral resolution for a recipient in any suitable manner. For example, fitting device 900 may be configured to perform various diagnostic tests to identify such regions.

In some examples, fitting device 900 and/or sound processor 204 may be configured to set a most comfortable level ("M level") for the phantom electrical stimulation applied by way of phantom stimulation channel 710. This may be performed in any suitable manner. For example, fitting device 900 and/or sound processor 204 may set the M level based on a CT scan of the cochlea, a bandwidth of lower region 704, an M level associated with one or more of electrodes 212, and/or any other factor as may serve a particular implementation.

In some examples, sound processor 204 may be configured to implement a frequency allocation table that does not include frequencies in lower region 704 (e.g., a frequency allocation table that defines the mapping illustrated in FIG.

7) in accordance with an acclimatization heuristic. For example, sound processor 204 may further maintain an initial frequency allocation table that maps frequencies in both upper region 702 and lower region 704 to electrodes 212 (e.g., as shown in FIG. 6). Sound processor 204 may initially direct the cochlear implant to apply standard electrical stimulation representative of frequencies in an audio signal that are within both upper region 702 and lower region 704 in accordance with the initial frequency allocation table. Sound processor 204 may gradually switch from using the initial frequency allocation table to using a frequency allocation table that does not include frequencies in lower region 704 (e.g., a frequency allocation table that defines the mapping illustrated in FIG. 7) over time in accordance with an acclimatization heuristic. The acclimatization heuristic may define incremental adaptions to the initial frequency allocation table such that, over time, sound processor 204 switches to using the frequency allocation table that does not include frequencies in lower region 704.

In some examples, fitting device 900 and/or sound processor 204 may perform one or more tests to predict recipient benefit after acclimatization. For example, one or more spectral ripple tests, behavioral tests, EEG measurements, and/or other types of tests may be performed by fitting device 900 and/or sound processor 204 with respect to the recipient to determine how well any of the stimulation schemes described herein are functioning. In response to the one or more tests, fitting device 900 and/or sound processor 204 may adjust one or more parameters associated with hearing system 100. For example, fitting device 900 and/or sound processor 204 may adjust cutoff frequency 706, one or more frequency-to-electrode mappings in a frequency allocation table, etc.

In some examples, sound processor 204 may use an own-voice detector to improve sound quality of a recipient's own voice. For example, sound processor 204 may detect when the recipient himself or herself is talking. In response, sound processor 204 may adjust cutoff frequency 706, one or more frequency-to-electrode mappings in a frequency allocation table, and/or any other parameter of hearing system 100 to enhance the sound quality of the recipient's own voice.

Figure 11:
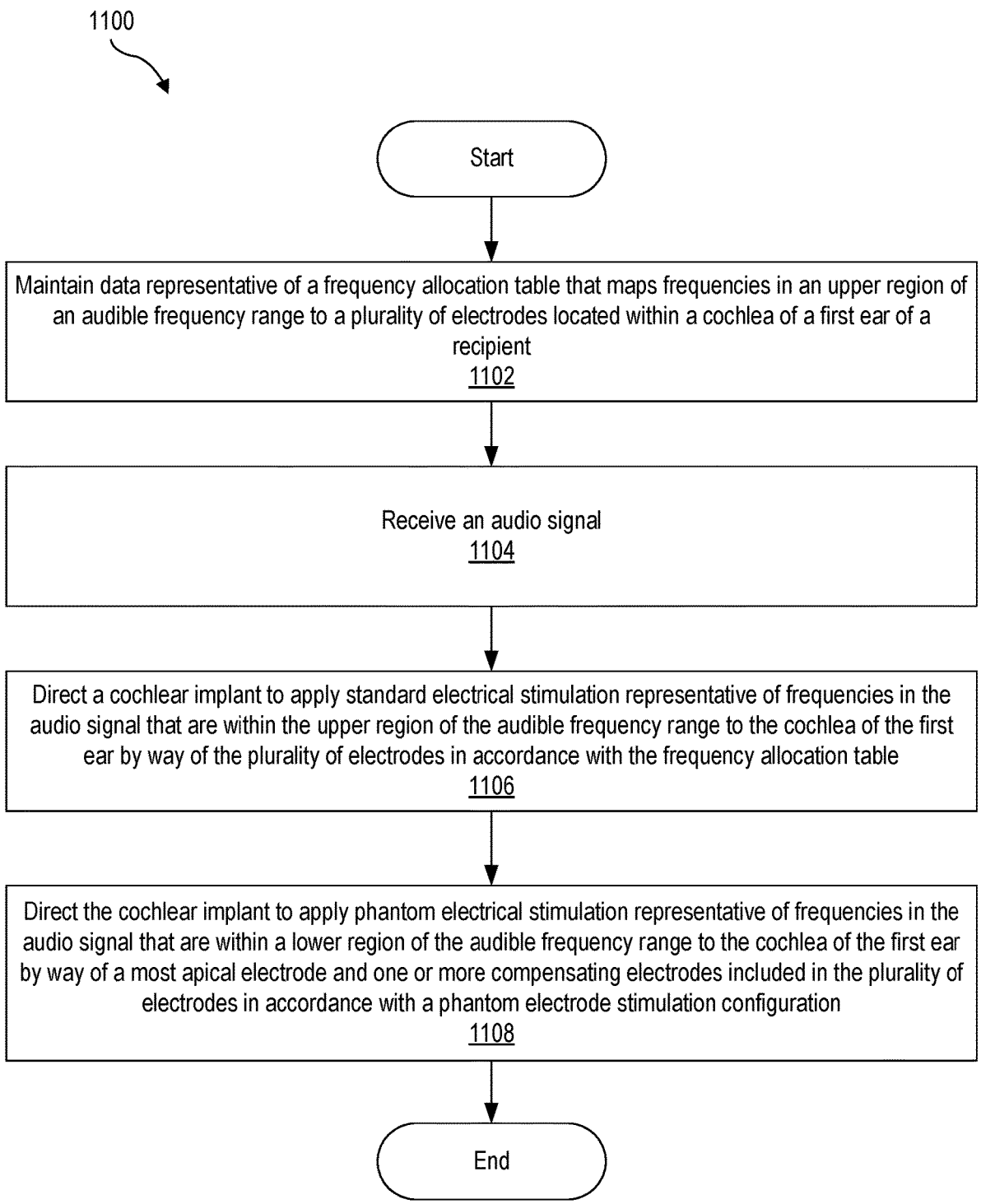
FIG. 11 illustrates an exemplary method according to principles described herein.

FIG. 11 illustrates an exemplary method 1100. The operations shown in FIG. 11 may be performed by sound processor 204 and/or any implementation thereof. While FIG. 11 illustrates exemplary operations according to one embodiment, other embodiments may omit, add to, reorder, and/or modify any of the operations shown in FIG. 11.

In operation 1102, a sound processor maintains data representative of a frequency allocation table that maps frequencies in an upper region of an audible frequency range to a plurality of electrodes located within a cochlea of a first ear of a recipient. Operation 1102 may be performed in any of the ways described herein.

In operation 1104, the sound processor receives an audio signal. Operation 1104 may be performed in any of the ways described herein.

In operation 1106, the sound processor directs a cochlear implant to apply standard electrical stimulation representative of frequencies in the audio signal that are within the upper region of the audible frequency range to the cochlea of the first ear by way of the plurality of electrodes in accordance with the frequency allocation table. Operation 1106 may be performed in any of the ways described herein.

In operation 1108, the sound processor directs the cochlear implant to apply phantom electrical stimulation representative of frequencies in the audio signal that are within a lower region of the audible frequency range to the cochlea of the first ear by way of a most apical electrode and one or more compensating electrodes included in the plurality of electrodes in accordance with a phantom electrode stimulation configuration. Operation 1108 may be performed in any of the ways described herein.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 12:
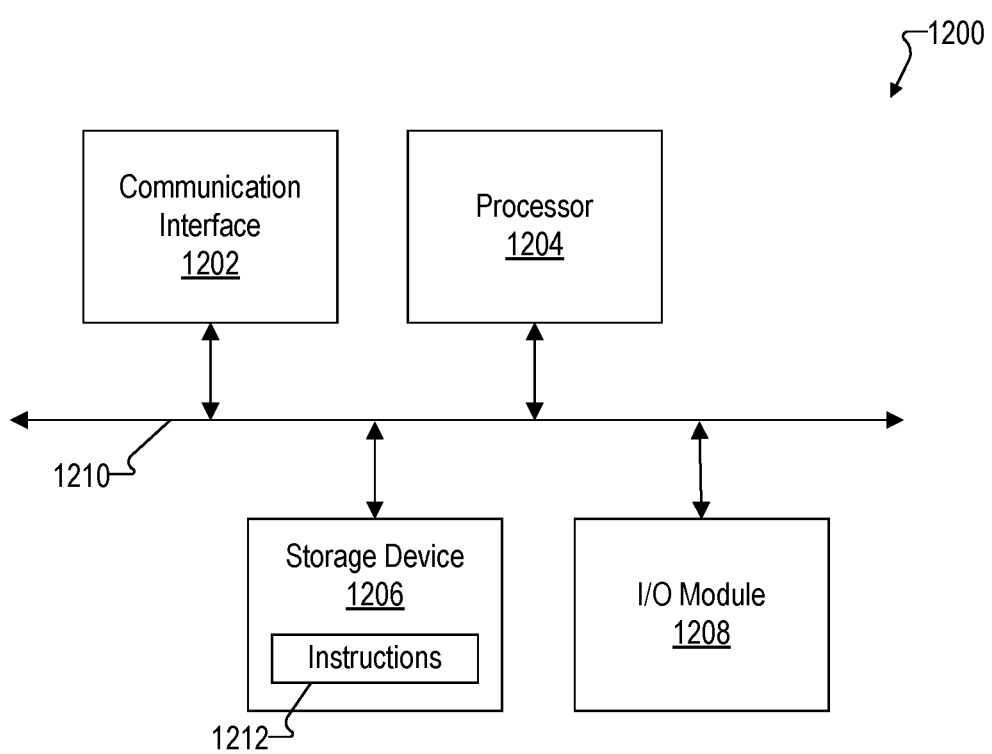
FIG. 12 illustrates an exemplary computing device according to principles described herein.

FIG. 12 illustrates an exemplary computing device 1200 that may be specifically configured to perform one or more of the processes described herein. As shown in FIG. 12, computing device 1200 may include a communication interface 1202, a processor 1204, a storage device 1206, and an input/output ("I/O") module 1208 communicatively connected one to another via a communication infrastructure 1210. While an exemplary computing device 1200 is shown in FIG. 12, the components illustrated in FIG. 12 are not intended to be limiting. Additional or alternative components may be used in other embodiments. Components of computing device 1200 shown in FIG. 12 will now be described in additional detail.

Communication interface 1202 may be configured to communicate with one or more computing devices. Examples of communication interface 1202 include, without limitation, a wired network interface (such as a network interface card), a wireless network interface (such as a wireless network interface card), a modem, an audio/video connection, and any other suitable interface.

Processor 1204 generally represents any type or form of processing unit capable of processing data and/or interpreting, executing, and/or directing execution of one or more of the instructions, processes, and/or operations described herein. Processor 1204 may perform operations by executing computer-executable instructions 1212 (e.g., an application, software, code, and/or other executable data instance) stored in storage device 1206.

Storage device 1206 may include one or more data storage media, devices, or configurations and may employ any type, form, and combination of data storage media and/or device. For example, storage device 1206 may include, but is not limited to, any combination of the non-volatile media and/or volatile media described herein. Electronic data, including data described herein, may be temporarily and/or permanently stored in storage device 1206. For example, data representative of computer-executable instructions 1212 configured to direct processor 1204 to perform any of the operations described herein may be stored within storage device 1206. In some examples, data may be arranged in one or more databases residing within storage device 1206.

I/O module 1208 may include one or more I/O modules configured to receive user input and provide user output. I/O module 1208 may include any hardware, firmware, software, or combination thereof supportive of input and output capabilities. For example, I/O module 1208 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1208 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1208 is configured to provide graphical data to a display for presentation to a user. The graphical data may be representative of one or more graphical user interfaces and/or any other graphical content as may serve a particular implementation.

In some examples, any of the systems, computing devices, and/or other components described herein may be implemented by computing device 1200. For example, storage facility 902 may be implemented by storage device 1206, and processing facility 904 may be implemented by processor 1204.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a sound processor associated with a first ear of a recipient and configured to:
  maintain data representative of a frequency allocation table that maps frequencies in an upper region of an audible frequency range to a plurality of electrodes located within a cochlea of the first ear, the upper region of the audible frequency range comprising frequencies above and including a cutoff frequency that corresponds to a place pitch of a most apical electrode included in the plurality of electrodes;
  receive an audio signal;
  direct a cochlear implant to apply standard electrical stimulation representative of frequencies in the audio signal that are within the upper region of the audible frequency range to the cochlea of the first ear by way of the plurality of electrodes in accordance with the frequency allocation table; and
  direct the cochlear implant to apply phantom electrical stimulation representative of frequencies in the audio signal that are within a lower region of the audible frequency range to the cochlea of the first ear by way of the most apical electrode and one or more compensating electrodes included in the plurality of electrodes in accordance with a phantom electrode stimulation configuration, the lower region of the audible frequency range comprising frequencies below the cutoff frequency.

2. The system of claim 1, further comprising:
a hearing device associated with a second ear of the recipient and configured to:
  receive the audio signal; and
  direct a receiver to apply, to the second ear, acoustic stimulation representative of the frequencies in the audio signal that are in the lower region of the audible frequency range.

3. The system of claim 1, wherein the sound processor is further configured to direct a receiver to apply, to the first ear, acoustic stimulation representative of the frequencies in the audio signal that are in the lower region of the audible frequency range.

4. The system of claim 1, further comprising a fitting device configured to:
  be communicatively coupled to the sound processor;
  specify the frequency allocation table; and
  transmit the data representative of the frequency allocation table to the sound processor.

5. The system of claim 4, wherein the fitting device is configured to specify the frequency allocation table by:
  setting a value for the cutoff frequency; and
  mapping the cutoff frequency to the most apical electrode.

6. The system of claim 5, wherein the fitting device is configured to set the value for the cutoff frequency by:
  accessing data representative of a computerized tomography (CT) scan of the cochlea;
  identifying, based on the CT scan, the place pitch of the most apical electrode; and
  designating the place pitch as the cutoff frequency.

7. The system of claim 4, wherein the fitting device is configured to specify the frequency allocation table by:
  identifying a frequency region within the audible frequency range that has poor spectral resolution for the recipient; and
  mapping frequencies within the frequency region to multiple electrodes included in the plurality of electrodes.

8. The system of claim 4, wherein at least one of the sound processor and the fitting device is configured to set an M level for the phantom electrical stimulation applied in accordance with the phantom electrode stimulation configuration.

9. The system of claim 8, wherein the setting of the M level is based on at least one of a computerized tomography (CT) scan of the cochlea, a bandwidth of the lower region, and an M level associated with one or more of the plurality of electrodes.

10. The system of claim 1, wherein:
the cutoff frequency is at least 700 Hz; and
the lower region includes frequencies between 250 Hz and the cutoff frequency.

11. The system of claim 1, wherein the directing of the cochlear implant to apply the phantom electrical stimulation representative of the frequencies in the audio signal that are within the lower region of the audible frequency range to the cochlea of the first ear in accordance with the phantom electrode stimulation configuration comprises:
  directing the cochlear implant to apply a main stimulation current by way of the most apical electrode;
  direct the cochlear implant to concurrently apply, while the main stimulation current is being applied by way of the most apical electrode, a compensation stimulation current by way of the one or more compensating electrodes, and optimizing an amount of the compensation stimulation current to result in the frequencies in the audio signal that are within the lower region of the audible frequency range being presented to the recipient.

12. The system of claim 11, wherein the compensation stimulation current is out of phase with the main stimulation current.

13. The system of claim 1, wherein the sound processor is further configured to:
maintain an initial frequency allocation table that maps frequencies in both the upper region and the lower region to the plurality of electrodes;
direct the cochlear implant to apply standard electrical stimulation representative of frequencies in the audio signal that are within both the upper region and the lower region to the cochlea of the first ear by way of the plurality of electrodes in accordance with the initial frequency allocation table;
gradually switch from using the initial frequency allocation table to using the frequency allocation table over time in accordance with an acclimatization heuristic.

14. The system of claim 1, wherein the sound processor is further configured to:
detect when the recipient is talking; and
adjust, in response to detecting when the recipient is talking, at least one of the cutoff frequency and a frequency-to-electrode mapping specified in the frequency allocation table.

15. A system comprising:
a first microphone configured to detect audio content presented to a recipient and output a first audio signal representative of the audio content;
a sound processor communicatively coupled to the first microphone and associated with a first ear of the recipient, the sound processor configured to:
maintain data representative of a frequency allocation table that maps frequencies in an upper region of an audible frequency range to a plurality of electrodes located within a cochlea of the first ear, the upper region of the audible frequency range comprising frequencies above and including a cutoff frequency that corresponds to a place pitch of a most apical electrode included in the plurality of electrodes;
receive, from the first microphone, the first audio signal;
direct a cochlear implant to apply standard electrical stimulation representative of frequencies in the first audio signal that are within the upper region of the audible frequency range to the cochlea of the first ear by way of the plurality of electrodes in accordance with the frequency allocation table; and
direct the cochlear implant to apply phantom electrical stimulation representative of frequencies in the first audio signal that are within a lower region of the audible frequency range to the cochlea of the first ear by way of the most apical electrode and one or more compensating electrodes included in the plurality of electrodes in accordance with a phantom electrode stimulation configuration, the lower region of the audible frequency range comprising frequencies below the cutoff frequency;
a second microphone configured to detect the audio content presented to the recipient and output a second audio signal representative of the audio content;
a hearing device associated with a second ear of the recipient and configured to:
receive, from the second microphone, the second audio signal; and
direct a receiver to apply, to the second ear, acoustic stimulation representative of frequencies in the second audio signal that are in the lower region of the audible frequency range.

16. A method comprising:
maintaining, by a sound processor associated with a first ear of a recipient, data representative of a frequency allocation table that maps frequencies in an upper region of an audible frequency range to a plurality of electrodes located within a cochlea of the first ear, the upper region of the audible frequency range comprising frequencies above and including a cutoff frequency that corresponds to a place pitch of a most apical electrode included in the plurality of electrodes;
receiving, by the sound processor, an audio signal;
directing, by the sound processor, a cochlear implant to apply standard electrical stimulation representative of frequencies in the audio signal that are within the upper region of the audible frequency range to the cochlea of the first ear by way of the plurality of electrodes in accordance with the frequency allocation table; and
directing, by the sound processor, the cochlear implant to apply phantom electrical stimulation representative of frequencies in the audio signal that are within a lower region of the audible frequency range to the cochlea of the first ear by way of the most apical electrode and one or more compensating electrodes included in the plurality of electrodes in accordance with a phantom electrode stimulation configuration, the lower region of the audible frequency range comprising frequencies below the cutoff frequency.

17. The method of claim 16, further comprising:
receiving, by a hearing device associated with a second ear of the recipient, the audio signal; and
directing, by the hearing device, a receiver to apply, to the second ear, acoustic stimulation representative of the frequencies in the audio signal that are in the lower region of the audible frequency range.

18. The method of claim 16, further comprising directing, by the sound processor, a receiver to apply, to the first ear, acoustic stimulation representative of the frequencies in the audio signal that are in the lower region of the audible frequency range.

19. The method of claim 16, wherein the directing of the cochlear implant to apply the phantom electrical stimulation representative of the frequencies in the audio signal that are within the lower region of the audible frequency range to the cochlea of the first ear in accordance with the phantom electrode stimulation configuration comprises:
directing the cochlear implant to apply a main stimulation current by way of the most apical electrode;
direct the cochlear implant to concurrently apply, while the main stimulation current is being applied by way of the most apical electrode, a compensation stimulation current by way of the one or more compensating electrodes, and
optimizing an amount of the compensation stimulation current to result in the frequencies in the audio signal that are within the lower region of the audible frequency range being presented to the recipient.

20. The method of claim 19, wherein the compensation stimulation current is out of phase with the main stimulation current.

* * * * *